United States Patent
Falkowski et al.

(10) Patent No.: US 10,307,747 B2
(45) Date of Patent: Jun. 4, 2019

(54) METAL ORGANIC FRAMEWORKS, THEIR SYNTHESIS AND USE

(71) Applicant: ExxonMobil Research and Engineering Company, Annandale, NJ (US)

(72) Inventors: Joseph M. Falkowski, Hampton, NJ (US); Mary S. Abdulkarim, Palisades Park, NJ (US); Mobae Afeworki, Phillipsburg, NJ (US); Randall J. Meyer, Clinton, NJ (US); Simon C. Weston, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/969,182

(22) Filed: May 2, 2018

(65) Prior Publication Data
US 2018/0318817 A1    Nov. 8, 2018

Related U.S. Application Data (60) Provisional application No. 62/610,590, filed on Dec. 27, 2017, provisional application No. 62/501,154, filed on May 4, 2017.

(51) Int. Cl.
| | |
|---|---|
| *B01J 31/16* | (2006.01) |
| *B01J 31/00* | (2006.01) |
| *B01J 20/22* | (2006.01) |
| *C07F 9/42* | (2006.01) |
| *C07F 9/38* | (2006.01) |

(Continued)

(52) U.S. Cl.
CPC ......... *B01J 31/1691* (2013.01); *B01J 20/226* (2013.01); *B01J 31/00* (2013.01); *C07C 1/24* (2013.01); *C07C 5/2293* (2013.01); *C07C 5/2562* (2013.01); *C07F 9/3843* (2013.01); *C07F 9/3856* (2013.01); *C07F 9/425* (2013.01); *C07C 2531/16* (2013.01); *C07C 2531/18* (2013.01); *C07C 2531/24* (2013.01)

(58) Field of Classification Search
None
See application file for complete search history.

(56) References Cited

U.S. PATENT DOCUMENTS

| | | |
|---|---|---|
| 8,071,063 B2 | 12/2011 | Reyes et al. |
| 8,314,245 B2 | 11/2012 | Yaghi et al. |

(Continued)

OTHER PUBLICATIONS

Deria et al., "MOF Functionalization via Solvent-Assisted Ligand Incorporation: Phosphonates vs Carboxylates", Inorg. Chem., 2015, 54, 2185-2192.

(Continued)

*Primary Examiner* — Daniel Berns
(74) *Attorney, Agent, or Firm* — Liza Negron; Amanda K. Norwood (57) ABSTRACT

A novel metal organic framework, EMM-42, is described having the structure of UiO-66 and comprising bisphosphonate linking ligands. EMM-42 has acid activity and is useful as a catalyst in olefin isomerization. Also disclosed is a process of making metal organic frameworks, such as EMM-42, by heterogeneous ligand exchange, in which linking ligands having a first bonding functionality in a host metal organic framework are exchanged with linking ligands having a second different bonding functionality in the framework.

16 Claims, 6 Drawing Sheets

(51) Int. Cl.
  *C07C 1/24* (2006.01)
  *C07C 5/22* (2006.01)
  *C07C 5/25* (2006.01)

(56) References Cited

U.S. PATENT DOCUMENTS

| 8,653,292 B2 | 2/2014 | Hafizovic et al. |
| 8,920,541 B2 | 12/2014 | Ni et al. |
| 2004/0192543 A1 | 9/2004 | Lin et al. |

OTHER PUBLICATIONS

Deria et al., "Perfluoroalkane Functionalization of NU-1000 via Solvent-Assisted Ligand Incorporation: Synthesis and CO2 Adsorption Studies", J. Am. Chem. Soc., 2013, 135, 16801-16804.
Gagnon et al., "Conventional and Unconventional Metal-Organic Frameworks Based on Phosphonate Ligands: MOFs and UMOFs", Chem. Rev., 2012, 112, 1034-1054.
Jiang et al., "Brosnsted Acidity in Metal-Organic Frameworks", Chem. Rev., 2015, 115, 6966-6997.
Karagiaridi et al., "Solvent-Assisted Linker Exchange: An Alternative to the De Novo Synthesis of Unattainable Metal-Organic Frameworks", Angew. Chem. Int. Ed., 2014, 53, 4530-4540.
Kim et al., "Postsynthetic Ligand and Cation Exchange in Robust Metal-Organic Frameworks", J. Am. Chem. Soc., 2012, 134, 18082-18088.
Taddei et al., "The first route to highly stable crystalline microporous zirconium phosphonate metal-organic frameworks", Chem. Commun., 2014, 50, 14831-14834.
The International Search Report and Written Opinion of PCT/US2018/030817 dated Sep. 20, 2018.
The International Search Report and Written Opinion of PCT/US2018/030825 dated Sep. 20, 2018.
Wang et al., "Sulfonated Microporous Organic-Inorganic Hybrids as Strong Bronsted Acids", JACS, 2003, 125, 10375-10383.
Clearfield et al., "Highly Porous Zirconium Aryldiphosphonates and Their Converstion to Strong Bronsted Acids", Jour of Solid State Chemistry, 2002, 167, 376-385.
Yang et al., "The Preparation and Ion-Exchange Properties of Zirconium Sulphophosphonates", Reactive Polymers, 1987, 5, 13-21.
Clearfield, "Inorganic ion Exchange Materials for Nuclear Waste Effluent Treatment", Proceedings of the Annual Symposium on Industrial Environmental Chemistry: Waste Minimization, College Station Texas, Mar. 24-26, 1992.
Ngo et al., "Molecular Building Block Approaches to Chiral Porous Zirconium Phosphonates for Asymmetric Catalysis", J. Mol. Catal. A: Chemical, 2004, 215, 177-186.
Kim et al., "Discovery, Development, and Functionalization of Zr(IV)-based Metal-Organic Frameworks", CrystEngComm, 2012, 14, 4096-4104.
Marshall et al., "Postsynthetic Modification of Zirconium Metal-Organic Frameworks", Eur. J. Inorg. Chem., 2016, 4310-4311.
Alberti et al., "Preparation and Characterization of Zirconium Phosphate Diphosphonates with the gamma-structure: a new class of covalently pillared compounds", Materials Chemistry and Physics, 1993, 35, 187-192.
Alberti et al., "Mechanism of the Topotactic Fromation of [gamma]-Zirconium Phosphate Covalently Pillared with Diphosphonate Groups", Inorganic Chemistry, 1998, 37, 4672-4676.
Shi et al., "Hydro-Ionothermal Synthesis of Lanthanide-Organic Frameworks with 1,4-Phenylenebis(methylene) diphosphonate", Crystal Growth & Design, 2008, 8, 3917-3920.
The International Search Report and Written Opinion of PCT/US2018/030833 dated Jul. 18, 2018.
Leng et al., "Rapid Synthesis of Metal-Organic Frameworks MIL-101 (Cr) Without the Addition of Solvent and Hydrofluoric Acid", Crystal Growth & Design, 2016, 16, 1168-1171.
Amghouz et al., "Organic-Inorganic Hybrids Assembled from Lanthanide and 1,4-Phenylenebis(phosphonate)", Crystal Growth & Design, 2011, 11, 5289-5297.
Morel, "Synthesis of Phosphine-Functionalized Metal-Organic Frameworks and Their Applications in Metal-Supported Catalysis", Doctoral Thesis ETH-Zurich, 2016.
Pal et al., "New Extra Large Pore Chromium Oxophenylphosphate: An Efficient Catalyst in Liquid Phase Partial Oxidation Reactions", The Open Catalysis Journal, 2009, 2, 156-162.
Pal et al., "Organic-inorganic hybrid supermicroporous chromium oxophenylphosphate with magnetic and catalytic properties", Journal of Magnetism and Magnetic Materials, 2014, 363, 210-216.

METAL ORGANIC FRAMEWORKS, THEIR SYNTHESIS AND USE

CROSS-REFERENCE TO RELATED APPLICATIONS

This application claims priority to U.S. Provisional Application No. 62/610,590 filed Dec. 27, 2017 and U.S. Provisional Application No. 62/501,154 filed May 4, 2017, both of which are herein incorporated by reference in their entirety.

FIELD

The present disclosure relates to metal organic frameworks (MOFs), to a particular novel MOF, designated herein as EMM-42, and to the synthesis of MOFs and their use, particularly in catalytic applications.

BACKGROUND

Metal-organic frameworks (MOFs) are a relatively new class of porous materials that are comprised of metal ion/oxide secondary building units (SBUs) interconnected by organic linking ligands. MOFs are characterized by low densities, high internal surface areas, and uniformly sized pores and channels. For example, U.S. Pat. No. 8,653,292 describes Zr MOFs having a surface area of at least 1020 $m^2/g$ or, if functionalized, having a surface area of at least 500 $m^2/g$. As a result of these advantageous properties, MOFs have been investigated extensively for applications in gas separation and storage, sensing, catalysis, drug delivery, and waste remediation. The wide array of potential applications for MOFs stem from the nearly infinite combination of organic ligands and secondary building units available. Regardless of this diversity, many materials have been left undiscovered due to limitations in the synthetic protocols typically employed for MOF synthesis. The relatively high temperatures and long crystallization times employed to synthesize metal-organic frameworks preclude the incorporation of sensitive moieties. Furthermore, the multiple conformations possible between the ligand and metal SBUs make predicting and directing structure challenging.

Recently a novel method of accessing new MOF materials from a starting host framework has been realized through the use of post-synthetic linker and ion exchange. This method, referred to in the literature as Solvent Assisted Ligand Exchange (SALE) or Post-Synthetic Exchange (PSE), is discussed by, for example, Karagiaridi, O.; Bury, W.; Mondloch, J. E.; Hupp, J. T.; Farha, O. K. in "Solvent-Assisted Linker Exchange: An Alternative to the De Novo Synthesis of Unattainable Metal-Organic Frameworks", Angew. Chem. Int. Ed. 2014, 53, 4530-4540. This technique has allowed for the development of novel materials which have thus far eluded researchers.

One example of the SALE process is disclosed in U.S. Pat. No. 8,920,541 using a species of MOF known as a zeolitic imidazolate framework or ZIF, as the host framework. In particular, the '541 patent discloses a method for exchanging the imidazolate linker in a zeolitic imidazolate framework composition, said method comprising the steps of: (a) providing a first zeolitic imidazolate framework composition having a tetrahedral framework comprising a general structure, $M^1$-$IM^a$-$M^2$, wherein $M^1$ and $M^2$ comprise the same or different metal cations, and wherein $IM^a$ is an imidazolate or a substituted imidazolate linking moiety; (b) providing a liquid composition comprising $IM^b$, wherein $IM^b$ is an imidazolate or a substituted imidazolate which is different from $IM^a$; and (c) contacting the first zeolitic imidazolate framework composition with the liquid composition under conditions sufficient to exchange at least a portion of $IM^a$ with at least a portion of $IM^b$ and to produce a second zeolitic imidazolate framework composition, $M^1$-$IM^c$-$M^2$, wherein $IM^c$ comprises $IM^b$, and wherein the framework type of the second zeolitic imidazolate framework composition is different from the framework type obtained when a zeolitic imidazolate framework composition is prepared by crystallizing a liquid reaction mixture comprising a solution of $M^1$, $M^2$ and $IM^b$. One notable result of this work was the complete exchange of 2-methylimidazole (mim) in ZIF-8 for 5-azabenzimidazole (5-abim) to isolate a novel ZIF framework, EMM-19, composed of 5-abim linkers connected to zinc tetrahedra in a sodalite (IZA code SOD) topology. Such topologies are discussed in the "Atlas of Zeolite Framework Types", Fifth edition, 2001. This particular structure had been hypothesized to be unobtainable due to the propensity of azabenzimidazole linkers to form ZIFs with LTA-type topologies. This discovery allowed for the development of materials with highly desirable $CO_2$ adsorption characteristics not observed in the nearly identical ZIF-7.

Another type of relevant post-synthetic transformation is Solvent Assisted Ligand Incorporation (SALI), in which functional moieties are grafted onto the ligands and/or secondary building units of MOFs. For example, Hupp and coworkers demonstrated that the treatment of the Zr-based framework, NU-1000, results in the dehydration and grafting of pendant carboxylate and phosphonate moieties onto the secondary building unit (See MOF Functionalization via Solvent-Assisted Ligand Incorporation: Phosphonates vs Carboxylates. Inorg. Chem. 2015, 54, 2185-2192 and Perfluoroalkane Functionalization of NU-1000 via Solvent-Assisted Ligand Incorporation: Synthesis and $CO_2$ Adsorption Studies. J. Am. Chem. Soc. 2013, 135, 16801-16804. Interestingly, this transformation occurs without loss of crystallinity of the parent material and serves to tune the adsorption properties of the resulting material.

Despite these advances, there remains a need for new methods of post-synthesis modification of MOF structures and particularly for those methods which allow the production of ligand/SBU combinations that are difficult or impossible to access by conventional MOF synthesis routes.

The present invention unexpectedly allows for the exchange of ligands in extremely kinetically inert frameworks such as those containing Cr(III) cations, which were discussed in Postsynthetic Ligand and Cation Exchange in Robust Metal—Organic Frameworks, J. Am. Chem. Soc. 2012, 134, 18082-18088, as not being viable for post synthetic ligand exchange.

SUMMARY

According to the present disclosure, it has now been found that linker exchange can be used with a MOF comprising a first organic linking ligand having a first bonding functionality to partially or completely replace the first ligand with a second organic linking ligand having a second bonding functionality different from the first binding functionality. In particular, it has been found that an organic linking ligand with monoprotic acid bonding functionality, such as a carboxylate ligand, can be partially or completely replaced with an organic linking ligand having polyprotic acid bonding functionality, such as a phosphonate ligand, to allow incorporation of acidic behavior in a MOF. Based on this technique a new MOF, designated as EMM-42, has been produced by exchange of the benzene-dicarboxylic acid linker in MIL 101(Cr) with a phenylene-bisphosphonic acid linker, also referred to herein as 1,4-phenylene-bis(phosphonic acid) linker. EMM-42 is an active catalyst for a variety of organic conversion reactions, including olefin isomerization. The terms "linker" and "ligand" can be used interchangeably herein. The present invention allows for oxidizing metal ions—such as Cr(III)—to be coupled with these phosphonic acid moieties. EMM-42 exhibits larger pore diameter of up to about 30 Å, the ability to couple metal-oxide catalytic centers capable of oxidation chemistry and stability in water and other environmentally benign solvents allowing for exchange in solvents such as water and ethanol.

In one aspect, the present disclosure resides in a metal organic framework having the structure of MIL-101(Cr) and comprising phenylene-bisphosphonic acid linking ligands, also referred to herein as 1,4-phenylene-bis(phosphonic acid) linking ligands.

In a further aspect, the present disclosure resides in a metal organic framework comprising trigonal nodes of 3 chromium atoms and at least 13 oxygen atoms partially or fully interconnected by phenylene-bisphosphonic acid linking ligands, also referred to herein as 1,4-phenylene-bis(phosphonic acid) linking ligands.

In yet a further aspect, the present disclosure resides in a process for exchanging an organic linking ligand in a metal organic framework, the process comprising:

(a) providing a first metal organic framework comprising a three-dimensional microporous crystal framework structure comprising metal-containing secondary building units connected by a first organic linking ligand comprising benzene-dicarboxylate acid ligands having a first bonding functionality with the secondary building units, (b) providing a liquid medium containing an organic compound capable of reacting with the secondary building units to act as a second organic linking ligands having a second bonding functionality with the secondary building units different from the first bonding functionality; and (c) contacting the first metal organic framework with the liquid medium under conditions effective for the organic compound to react with the secondary building units in the first metal organic framework and exchange at least some of the first organic linking ligands with second organic linking ligands and produce a second metal organic framework.

In some embodiments, the first organic linking ligand is bonded to each secondary building unit through a monoprotic acid group and the second organic linking ligand is bonded to each secondary building unit through a polyprotic acid group.

In another aspect, the present disclosure resides in an organic compound conversion process, such as an olefin isomerization process, comprising contacting an organic compound-containing feed with a catalyst comprising the metal organic framework described herein.

DETAILED DESCRIPTION OF THE EMBODIMENTS

Disclosed herein is a novel metal organic framework, designated EMM-42, which has the structure of MIL-101 (Cr) and comprises phenylene-bisphosphonic acid linking ligands, also referred to herein as 1,4-phenylene-bis(phosphonic acid) linking ligands, optionally together with dicarboxylate linking ligands, and its use as a catalyst. Also disclosed is a process for producing metal organic frameworks, such as EMM-42, by heterogeneous ligand exchange. In this process, first organic linking ligands interconnecting secondary building units (SBUs) in a host metal organic framework through a first bonding functionality are partially or completely replaced by second organic linking ligands which bond to the SBUs through a second, different functionality.

MIL-101(Cr) is a metal organic framework composed of trigonal nodes of 3 chromium and at least 13 oxygen atoms that are bridged by benzene-dicarboxylate linkages in the MTN (IZA code) topology. MIL-101(Cr) is reported to have an X-ray diffraction pattern which includes the characteristic lines listed in Table 1 below:

TABLE 1

| Interplanar d-Spacing (Å) | Two-theta | Relative Intensity (100 × I/Io) |
|---|---|---|
| 30.9764 | 2.85 | 33.2 |
| 26.7035 | 3.306 | 100 |
| 22.2394 | 3.97 | 21.2 |
| 20.3777 | 4.333 | 8.7 |
| 18.1352 | 4.869 | 18.2 |
| 17.0936 | 5.166 | 48.6 |
| 15.6749 | 5.634 | 19.9 |
| 14.9958 | 5.889 | 39.8 |
| 14.0302 | 6.295 | 2.3 |
| 13.527 | 6.529 | 4.1 |
| 10.8524 | 8.14 | 8.9 |
| 10.469 | 8.439 | 43.6 |
| 10.2609 | 8.611 | 21.2 |
| 9.7499 | 9.063 | 67 |
| 9.0681 | 9.746 | 5.8 |
| 8.7083 | 10.149 | 4.1 |
| 8.5493 | 10.339 | 9.5 |
| 7.85 | 11.263 | 5 |
| 7.533 | 11.738 | 3.6 |
| 5.6984 | 15.538 | 2.9 |

Figure 1:
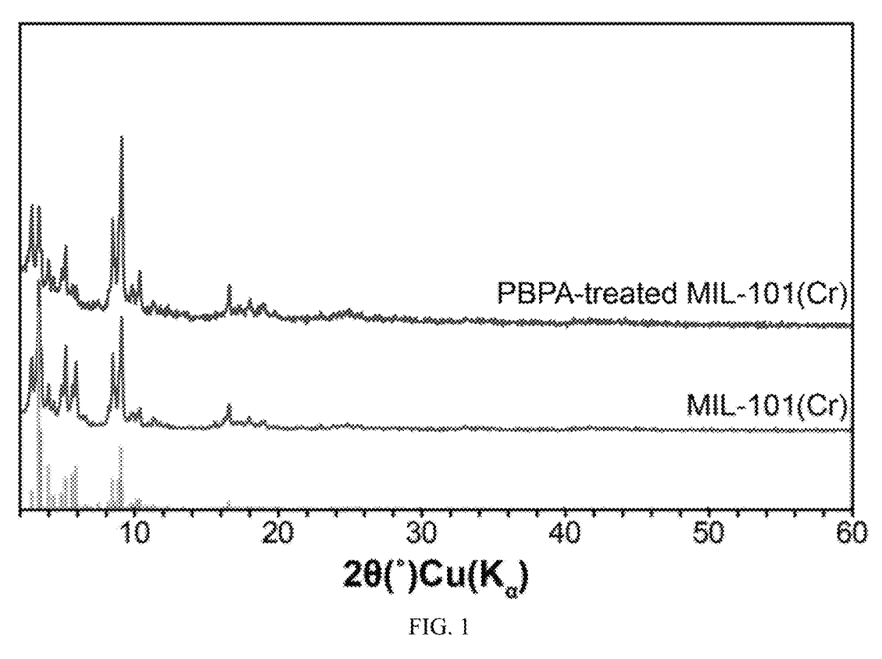
FIG. 1 shows the powder X-ray diffraction patterns of a MIL-101(Cr) and MIL-101(Cr) after partial exchange with phenylene-bisphosphonic acid, also referred to herein as 1,4-phenylene-bis(phosphonic acid), ($H_4$-PBPA).
Figure 2:
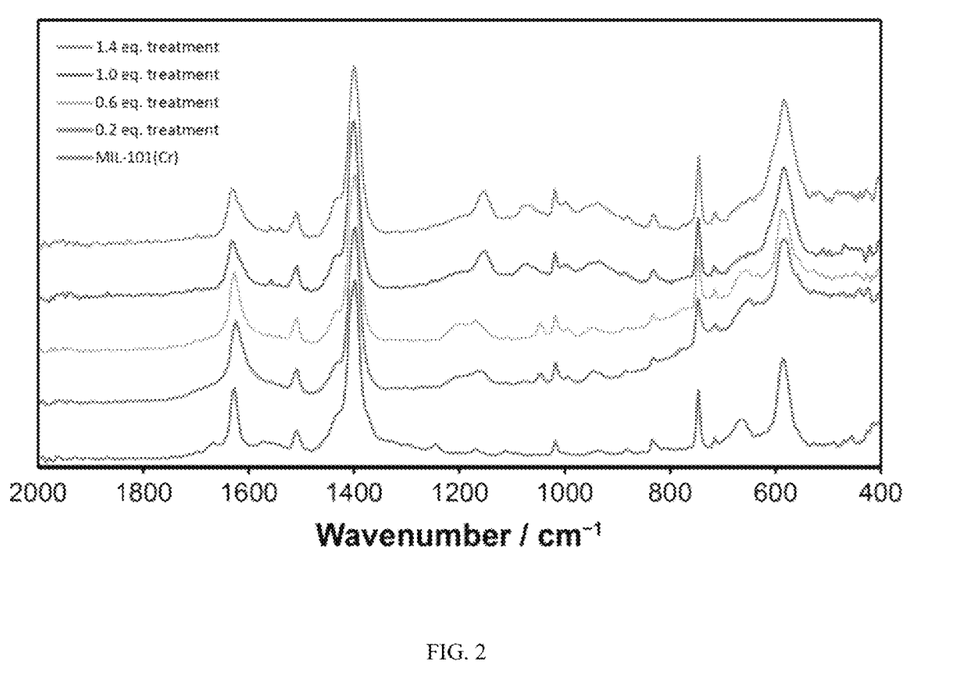
FIG. 2 shows the ATR-IR spectra of MIL-101(Cr) [lowermost graph] and MIL-101(Cr) after treatment with various amounts of phenylene-bisphosphonic acid ($H_4$-PBPA).
Figure 3:
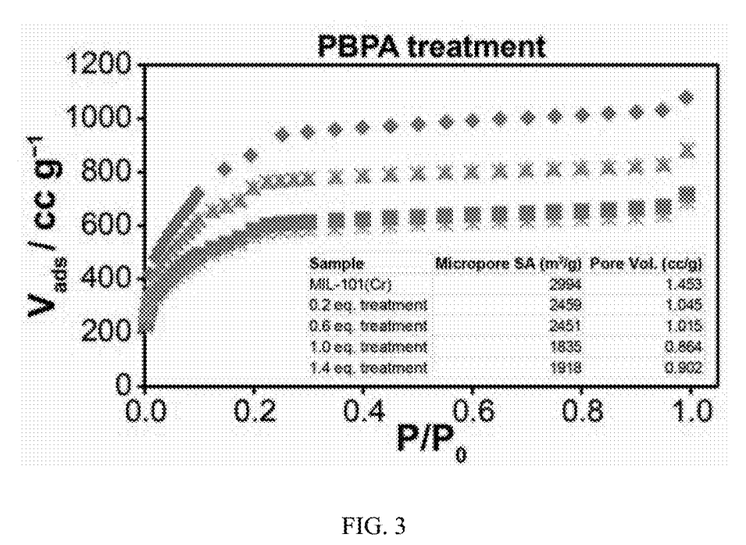
FIG. 3 shows the $N_2$ gas adsorption curves conducted at 77K of a MIL-101(Cr) starting material and its phosphonate-exchanged products after reaction with 0.2, 0.6, 1.0 and 1.4 mol. equivalents of phenylene-bisphosphonic acid also referred to herein as 1,4-phenylene-bis(phosphonic acid), ($H_4$-PBPA). Inset lists the micropore surface area and micropore volumes.

EMM-42 is a metal organic framework having the same SBUs as MIL-101(Cr), namely trigonal nodes of 3 chromium atoms, in which some or all of the benzene-dicarboxylate ligands joining adjacent chromium nodes have been exchanged by phenylene-bisphosphonic acid linking ligands. EMM-42 is isostructural with MIL-101(Cr) and so generally has a similar characteristic X-ray diffraction pattern as MIL-101(Cr). As shown in FIG. 1, there is nominal difference in crystallinity. In some embodiments, therefore, it may be desirable to control the ligand exchange so that no more than 50%, such as no more than 30%, for example no more than 20% of the benzene-dicarboxylate acid ligands in the MIL-101(Cr) parent material are replaced by 1,4-phenylene ligands. Typically, at least 5% of the benzene-dicarboxylic acid ligands in the MIL-101(Cr) parent material are replaced by phenylene-bisphosphonic acid linking ligands.

One important difference between EMM-42 and MIL-101(Cr) concerns the nature of the bonding functionality of the different ligands. Thus, in MIL-101(Cr) the bonding to each $Cr_3O_{13}$ trigonal prism is via a monoprotic carboxylic acid group so that in the final MOF there is little or no remaining acid functionality. In contrast, in EMM-42 the bonding to each $Cr_3O_{13}$ trigonal prism is via a diprotic phosphonic acid group so that the final MOF has acid functionality and, as will be discussed in more detail below, exhibits catalytic activity for organic conversion reactions, such as olefin isomerization. By suitable functionalization on one or more of the phenyl groups of phenylene-bisphosphonate ligands, such as with electron withdrawing groups, this acidity can be increased, potentially with an increased catalytic activity of the final MOF. Suitable electron withdrawing groups include fluoro, chloro, bromo, iodo and nitro groups.

The process used to produce EMM-42 potentially has wide application in MOF synthesis and involves solvent assisted ligand exchange of a host MOF including first organic ligands having a first SBU bonding functionality by reaction in a liquid medium with an organic compound capable of reacting with the SBUs of the host MOF to produce second organic linking ligands having a second bonding functionality with the SBUs different from the first bonding functionality. Of course in the case of EMM-42 synthesis, the host MOF is MIL-101(Cr) having chromium SBUs interconnected by linking ligands having two monoprotic carboxylic acid groups and the replacing ligands have two diprotic phosphonic acid groups. However, the process is equally applicable to MOFs having different SBUs, including other metal ion/oxide-containing groups, especially groups comprising at least one trivalent metal, such as chromium, iron, vanadium and/or aluminum. Similarly, the process is applicable to host MOFs containing other organic linking ligands than benzene-dicarboxylic acid ligands, including other aromatic or non-aromatic dicarboxylate ligands, as well as ligands whose bonding functionality is not limited to monoprotic acid functionality, including, for example, zeolitic imidazolate frameworks or ZIFs and pyridine-containing frameworks. Further, the process can be used with other exchange ligands than bisphosphonate ligands, whether or not having a polyprotic acid bonding functionality, such as sulfonates and boronates.

In the linker exchange process described herein, a first or host metal organic framework (MOF) is provided in which the host MOF comprises a three-dimensional microporous crystal framework structure comprising metal-containing secondary building units connected by first organic linking ligands having a first bonding functionality with the secondary building units. In some embodiments, it may be desirable to remove unreacted species or impurities from the as-synthesized form of host MOF prior to linker exchange. These unreacted species or impurities may be removed by appropriate techniques, e.g., involving washing and drying. For example, the as-synthesized form of the host MOF may be washed with a suitable solvent, such as DMSO, followed by solvent exchange with ethanol, acetonitrile, or the like, decanting solvent and drying, for example, under vacuum at about 200° C.

In another step of the process, a liquid medium is provided containing an organic linker compound capable of reacting with the secondary building units in the host MOF to produce second organic linking ligands having a second bonding functionality with the secondary building units different from the first bonding functionality. For example, the first bonding functionality may be via a monoprotic acid functionality whereas the second bonding functionality may be via a polyprotic, such as a diprotic, acid functionality. The organic linker compound may be present in the liquid medium, for example, in the form of the protonated form of the linker composition and/or in the form of a salt of the composition.

The liquid medium may comprise a solution of the organic linker compound in a solvent. The solvent may be a polar organic solvent, such as N,N-dimethylformamide (DMF), N,N-diethylformamide (DEF), N,N-dimethylacetamide (DMAc), 1,3-dimethylpropyleneurea (DMPU), a sulfoxide (e.g., dimethylsulfoxide or DMSO), a phosphoramide (e.g., hexamethylphosphoramide), an alcohol (e.g. butanol), acetonitrile (MeCN), triethylamine (TEA), or a combination thereof. Alternatively, though not strictly organic, aqueous solvents such as aqueous ammonia and ethanol mixtures, can be used as solvents for the linker compound(s).

Though polar organic compounds such as N,N-dimethylformamide (DMF) are suggested as solvents herein, it should be understood that a solvent (or solvent system) useful in the methods according to the invention and/or useful in making products according to the invention should at least be able to solvate and/or solubilize the reactants to the extent necessary to allow reaction to occur at a reasonable rate (or over a reasonable reaction time). They can also typically be present in a substantially liquid phase at operating/reaction conditions (and optionally but preferably also at STP).

In certain embodiments, solvents (and/or solvent systems) particularly useful in the invention can additionally or alternately exhibit a relatively high vapor pressure and/or a relatively low boiling point. For instance, in some such embodiments, a relatively high vapor pressure can represent at least 2.5 kPa at about 20° C., for example at least about 3.0 kPa at about 20° C., at least about 3.5 kPa at about 20° C., at least about 4.0 kPa at about 20° C., at least about 4.5 kPa at about 20° C., at least about 5.0 kPa at about 20° C., at least about 5.5 kPa at about 20° C., at least about 6.0 kPa at about 20° C., at least about 6.5 kPa at about 20° C., at least about 7.0 kPa at about 20° C., at least about 7.5 kPa at about 20° C., at least about 8.0 kPa at about 20° C., at least about 8.5 kPa at about 20° C., at least about 9.0 kPa at about 20° C., or at least about 9.5 kPa at about 20° C. Optionally, if an upper boundary on vapor pressure is needed and/or desired, the relatively high vapor pressure can be about 30 kPa or less at about 20° C., e.g., about 25 kPa or less at about 20° C., about 20 kPa or less at about 20° C., about 15 kPa or less at about 20° C., or about 10 kPa or less at about 20° C. Additionally or alternately, in some such embodiments, a relatively low boiling point can represent 99° C. or less, e.g., about 98° C. or less, about 96° C. or less, about 95° C. or less, about 93° C. or less, about 91° C. or less, about 90° C. or less, about 88° C. or less, about 86° C. or less, about 85° C. or less, about 83° C. or less, about 81° C. or less, or about 80° C. or less. Optionally, if a lower boundary on boiling point is needed and/or desired (preferably, the solvent can have a boiling point above ambient temperature, so as to be in a liquid phase), the relatively low boiling point can be at least about 25° C., e.g., at least about 30° C., at least about 35° C., at least about 40° C., at least about 45° C., at least about 50° C., at least about 55° C., at least about 60° C., at least about 65° C., at least about 70° C., at least about 75° C., or at least about 80° C. One such non-limiting example of a solvent system having both a relatively low boiling point and a relatively high vapor pressure includes a mixture of acetonitrile and triethylamine.

In another step of the present process, the host MOF is contacted with the liquid medium comprising organic linker compound. This contact may take place by combining (1) the host MOF, (2) the solvent, and (3) a source of organic linker compound in any order. For example, host MOF and organic linker compound may first be combined, and the solvent may be added to this combination, accomplishing the simultaneous formation of a liquid medium comprising the organic linker compound and contact of this composition with the host MOF. In a convenient embodiment, the source of organic linker compound can first be dissolved in the solvent, and either the resulting solution can be added to the host MOF or the host MOF can be added to the solution.

The amount of organic linking ligand used in the contacting step may be selected so that the molar ratio of the organic linking compound to first organic linking ligand in the host MOF is from 0.01 to 10, e.g., from 0.02 to 5, from 0.03 to 2, from 0.04 to 2, from 0.05 to 1, from 0.1 to 0.8, from 0.1 to 0.7, from 0.1 to 0.6, from 0.1 to 0.5, from 0.1 to 0.4. In particular, where less than complete exchange of the first organic linking ligand is desired, the molar ratio of the organic linking compound to first organic linking ligand in the host MOF is advantageously below 1, or alternatively below 0.5.

The combined mixture of the host MOF with the liquid medium comprising the organic linking compound can be maintained under conditions sufficient to achieve at least partial exchange of the first linking ligand with the second linking ligand and produce the second MOF. The contact may take place for a sufficient time to achieve at least partial exchange, e.g., from at least 1 hour to as much as 10 days, from 1 hour to 7 days, from 1 hour to 5 days, from 1 hour to 3 days, from 2 hours to 10 days, from 2 hours to 7 days, from 2 hours to 5 days, from 2 hours to 3 days, from 4 hours to 10 days, from 4 hours to 7 days, from 4 hours to 5 days, from 4 hours to 3 days, from 8 hours to 10 days, from 8 hours to 7 days, from 8 hours to 5 days, from 8 hours to 3 days, from 12 hours to 10 days, from 12 hours to 7 days, from 12 hours to 5 days, from 12 hours to 3 days, from 18 hours to 10 days, from 18 hours to 7 days, from 18 hours to 5 days, from 18 hours to 3 days, from 24 hours to 10 days, from 24 hours to 7 days, from 24 hours to 5 days, or from 24 hours to 3 days. The temperature of the combined mixture of the host MOF with the liquid medium comprising the organic linking compound may range, for example, from a temperature of about −78° C. (dry-ice bath temperature) to the boiling temperature of the solvent (the normal boiling point of N,N-dimethylformamide is about 153° C. and of dimethylsulfoxide is about 189° C.), from about 0° C. (ice water bath temperature) to at least 10° C. below the boiling temperature of the solvent, or from about 15° C. to at least 15° C. below the boiling temperature of the solvent (or alternately to about 100° C.). When contact takes place in a pressurized vessel, the temperature may exceed the boiling temperature of the solvent. For example, the contact may take place at room temperature or greater, such as from about 18° C. to about 200° C. or from about 75° C. to about 150° C.

After the contacting is complete, the second MOF may be recovered and treated, if necessary or desired (e.g., to remove molecules from the pore space of the second MOF). This treatment may involve techniques for activating the as-synthesized form of a MOF prepared by solvothermal methods, for example, as described in U.S. Pat. Nos. 8,314,245 and 8,071,063. For example, the recovered MOF may be washed and then solvent exchanged with acetonitrile and dried. Finally the dried acetonitrile-exchanged product may be placed under vacuum, e.g., less than about 10 mTorr at about 180° C. for about 18 hours, to yield the activated form of the MOF.

Depending on the nature of the second organic linking ligands and, if still partially present, the first organic linking ligands, the resultant activated second MOF may have a variety of uses, such as an adsorbent for gases such as hydrogen, nitrogen, oxygen, inert gases, carbon monoxide, carbon dioxide, sulfur dioxide, sulfur trioxide, hydrogen sulfide, ammonia, methane, natural gas, hydrocarbons and amines. In addition, where, as with EMM-42, the second MOF has acid functionality, other potential uses are in organic compound conversion reactions. Thus, in the case of EMM-42, one such catalytic use is in catalytic olefin isomerization, namely in shifting the position of the double bond in a $C_{3+}$ olefin, for example converting 2-methyl-2-pentene to 2-methyl-1-pentene. Such a process can, for example, be conducted by contacting a source of the olefin to be isomerized with EMM-42 at a temperature from about 200° C. to about 400° C., such as from about 250° C. to about 350° C.

The invention can additionally or alternatively include one or more of the following embodiments.

Embodiment 1. A metal organic framework having the structure of MIL-101(Cr) and comprising phenylene-bisphosphonic acid linking ligands.

Embodiment 2. The metal organic framework of embodiment 1 wherein the phenylene-bisphosphonic linking ligand is a tetrafluorophenylene-bisphosphonic acid linking ligand.

Embodiment 3. The metal organic framework of embodiment 1 or embodiment 2, wherein the metal organic framework comprises at least one trivalent metal.

Embodiment 4. The metal organic framework of embodiment 3, wherein the at least one trivalent metal is selected from the group consisting of chromium, iron, aluminum, vanadium and combinations thereof.

Embodiment 5. A metal organic framework comprising trigonal nodes of 3 chromium atoms and at least 13 oxygen atoms partially or fully interconnected by phenylene-bisphosphonic linking ligands.

Embodiment 6. The metal organic framework of embodiment 5, wherein the phenylene-bisphosphonic linking ligand is a tetrafluorophenylene-bisphosphonic ligand.

Embodiment 7. The metal organic framework of embodiment 5 or embodiment 6, wherein at least one of the phenyl groups of the phenylene-bisphosphonic ligand is substituted with one or more electron withdrawing groups.

Embodiment 8. The metal organic framework of embodiment 5, embodiment 6 or embodiment 7, wherein the metal organic framework comprises at least one trivalent metal.

Embodiment 9. The metal organic framework of embodiment 8, wherein the at least one trivalent metal is selected from the group consisting of chromium, iron, aluminum, vanadium and combinations thereof.

Embodiment 10. The metal organic framework of any of the preceding claims, further comprising a pore diameter of up to about 30 Å.

Embodiment 11. A process for exchanging an organic linking ligand in a metal organic framework of embodiment 1, the process comprising:
(a) providing a first metal organic framework comprising a three-dimensional microporous crystal framework structure comprising metal-containing secondary building units connected by first organic linking ligands comprising a benzene-dicarboxylate having a first bonding functionality with the secondary building units,
(b) providing a liquid medium containing an organic compound capable of reacting with the secondary building units to produce second organic linking ligands having a second bonding functionality with the secondary building units different from the first bonding functionality; and
(c) contacting the first metal organic framework with the liquid medium under conditions effective for the organic compound to react with the secondary building units in the first metal organic framework and exchange at least some of the first organic linking ligands with second organic linking ligands and produce a second metal organic framework.

Embodiment 12. The process of embodiment 11, wherein the first organic linking ligand is bonded to each secondary building unit through a monoprotic acid group.

Embodiment 13. The process of embodiment 11 or embodiment 12, wherein the second organic linking ligand is bonded to each secondary building unit through a polyprotic acid group.

Embodiment 14. The process of embodiment 11, embodiment 12 or embodiment 13, wherein the second organic linking ligand is bonded to each secondary building unit through a diprotic acid group.

Embodiment 15. The process of embodiment 11, embodiment 12, embodiment 13 or embodiment 14, wherein the second organic linking ligand comprises a phenylene-bisphosphonic acid.

Embodiment 16. The process of embodiment 15, wherein the second organic linking ligand comprises tetrafluorophenylene-bisphosphonic acid.

Embodiment 17. The process of embodiment 11, embodiment 12, embodiment 13, embodiment 14, embodiment 15 or embodiment 16, wherein the secondary building units comprise at least one trivalent metal.

Embodiment 18. The process of embodiment 17, wherein the secondary building units at least one trivalent metal is selected from the group consisting of chromium, iron, aluminum, vanadium and combinations thereof.

Embodiment 19. The process of embodiment 11, embodiment 12, embodiment 13, embodiment 14, embodiment 15, embodiment 16 or embodiment 17, wherein the second metal organic framework is isostructural with the first metal organic framework.

Embodiment 20. The process of embodiments 11 to 19, wherein the first metal organic framework has the structure of MIL-101(Cr).

Embodiment 21. An organic compound conversion process comprising contacting an organic compound-containing feed with a catalyst comprising the metal organic framework of embodiments 1 to 10.

Embodiment 22. An olefin isomerization process comprising contacting an olefin-containing feed with a catalyst comprising the metal organic framework of any one of embodiments 1 to 10.

The invention will now be more particularly described with reference to the following non-limiting Examples and the accompanying drawings.

The X-ray diffraction data reported in the Examples were collected with a Bruker D8 Endeavor diffraction system with an lynxeye detector, using copper K-alpha radiation. The diffraction data were recorded by step-scanning at 0.02 degrees of two-theta, where theta is the Bragg angle, and using an effective counting time of 2 seconds for each step.

Example 1: Ligand Exchange of Phenylene-Bisphosphonic Acid, Also Referred to as 1,4-Phenylene-Bis(Phosphonic Acid), ($H_4$-PBPA) into MIL-101 (Cr)

2 g of MIL-101 (Cr) was suspended in 150 mL of dimethylsulfoxide (DMSO), to this, 2 g of $H_4$-PBPA was added. The reaction was then heated with stirring for 3 days at 150° C. Upon completion, the reaction was filtered and washed by stirring in DMSO at 150° C. for an additional day. The solids were isolated by filtration and washed by solvent extraction with acetonitrile overnight. FIG. 1 shows the resulting X-ray diffraction pattern.

Example 2: Ligand Exchange of tetrafluorophenylene-bisphosphonic acid ($F_4$-PBPA) into MIL-101(Cr)

Figure 4:
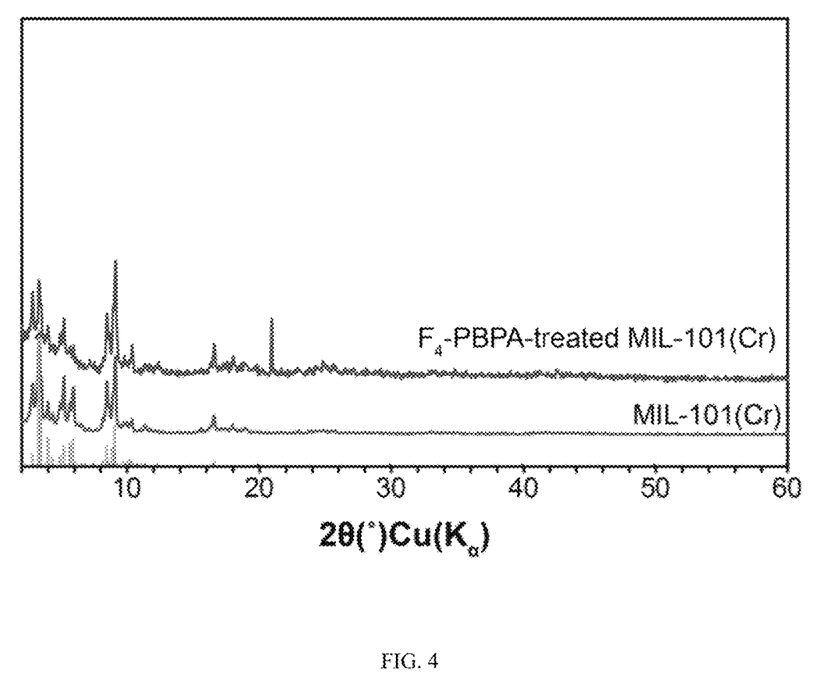
FIG. 4 shows the powder X-ray diffraction patterns conducted on MIL-101(Cr) and MIL-101(Cr) after partial linker exchange with perfluoro-1,4-phenylene-bis(phosphonic acid), ($F_4$-PBPA).
Figure 5:
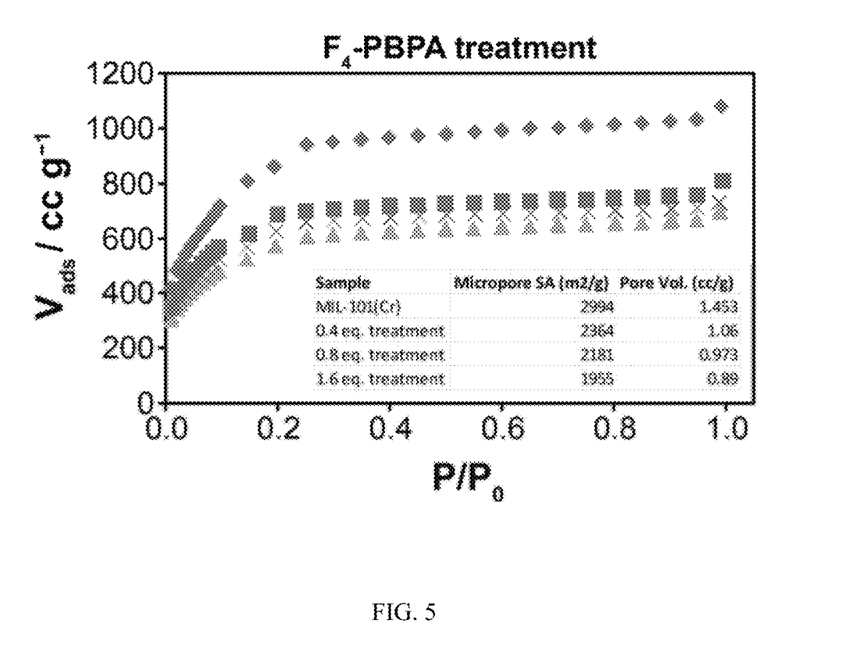
FIG. 5 shows the $N_2$ gas adsorption curves conducted at 77K of a MIL-101(Cr) starting material and its phosphonate-exchanged products after reaction with 0.4, 0.8 and 1.6 mol. equivalents of with perfluoro-1,4-phenylene-bis(phosphonic acid), ($F_4$-PBPA). Inset lists the micropore surface area and micropore volumes.
Figure 6:
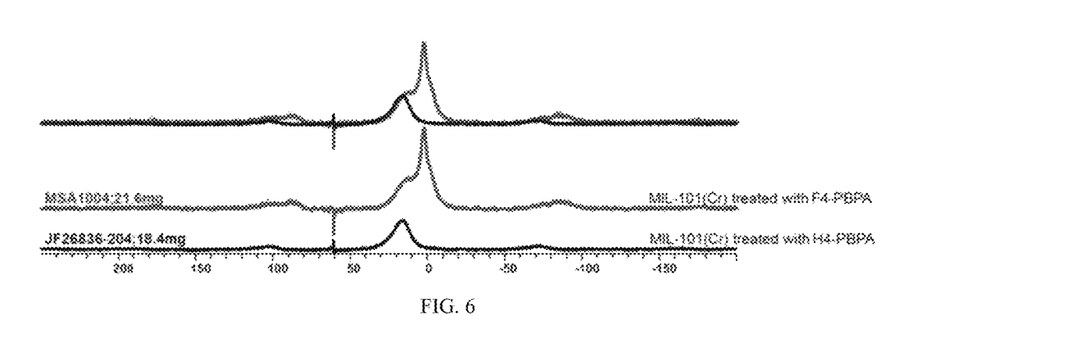
FIG. 6 shows the $^{31}P$ MAS NMR of MIL-101(Cr) after treatment with $H_4$-PBPA (lower graph) and $F_4$-PBPA (middle graph). The top graph is an overlay of the two spectra.

1.75 g of MIL-101 (Cr) was suspended in 150 mL of dimethylsulfoxide (DMSO), to this, 3.5 g of tetrafluorophenylene-bisphosphonic acid was added. The reaction was then heated and stirred for 3 days at 150° C. Upon completion, the reaction was filtered and washed by stirring in dimethylsulfoxide (DMSO) at 150° C. for an additional day. The solids were isolated by filtration and washed by solvent extraction with acetonitrile overnight. FIG. 4 shows the resulting X-ray diffraction pattern.

Example 3: Catalytic Testing of Materials Generated in Examples 1 and 2

A series of tests of the catalytic activity of the MIL-101 parent material and the EMM-42 produced in Examples 1 and 2 for the isomerization of 2-methyl-2-pentene (2MP=2) were conducted at temperatures of 250° C. and 350° C. The results are shown in Tables 2, 3 and 4 respectively, where all product composition values are in wt. % and the following abbreviations are used:
3MP=1,4MP=1 designates the total amount of 3-methyl-1-pentene and 4-methyl-1-pentene;
4MP=2 designates the total amount of cis- and trans-4-methyl-2-pentene;
2MP=1 designates 2-methyl-1-pentene;
3MP=2 designates the total amount of cis- and trans-3-methyl-2-pentene;
23DMB=1 designates 2,3-dimethyl-1-butene;
23DMB=2 designates 2,3-dimethyl-2-butene;
2EB=1 designates 2-ethyl-1-butene; and
t-2H=designates trans 2-hexene, no cis isomer having been detected.

From Tables 2, 3 and 4, it will be seen that MIL-101(Cr) showed only mild catalytic activity for the isomerization of 2MP=1 and 2MP=2, while the phosphonate-exchanged materials MIL-101(Cr) demonstrated moderate isomerization activity as evidenced by the production of 23DMB=1 and 23DMB=2, for example.

TABLE 2

Isomerization of 2-methyl-2-pentene by MIL-101(Cr)

| Time/hr | Temp. | $C_1$-$C_5$ | 4MP = 1 | c-4MP = 2 | t-4MP = 2 | 2MP = 1 | 2MP = 2 | c-3MP = 2 | t-3MP = 2 | 23DMB = 1 | 23DMB = 2 | 2EB = 1 | t-2H = |
|---|---|---|---|---|---|---|---|---|---|---|---|---|---|
| 0.08 | 250 | 0.000 | 0.013 | 0.060 | 0.262 | 16.133 | 83.092 | 0.039 | 0.024 | 0 | 0 | 0 | 0 |
| 1 | 250 | 0.099 | 0.000 | 0.000 | 0.014 | 4.030 | 95.029 | 0.021 | 0.013 | 0 | 0 | 0 | 0 |
| 2 | 350 | 0.147 | 0.011 | 0.042 | 0.170 | 11.858 | 86.535 | 0.037 | 0.021 | 0 | 0 | 0 | 0 |
| 3 | 250 | 0.099 | 0.000 | 0.000 | 0.011 | 2.530 | 96.420 | 0.021 | 0.012 | 0 | 0 | 0 | 0 |

TABLE 3

Isomerization of 2-methyl-2-pentene by MIL-101(Cr) with $H_4$-PBPA

| Time/hr | Temp. | $C_1$-$C_5$ | 4MP = 1 | c-4MP = 2 | t-4MP = 2 | 2MP = 1 | 2MP = 2 | c-3MP = 2 | t-3MP = 2 | 23DMB = 1 | 23DMB = 2 | 2EB = 1 | t-2H = |
|---|---|---|---|---|---|---|---|---|---|---|---|---|---|
| 0.08 | 250 | 0.092 | 1.686 | 2.613 | 10.355 | 21.787 | 57.072 | 0.803 | 1.285 | 0.592 | 1.679 | 0.166 | 0.050 |
| 1 | 250 | 0.037 | 0.101 | 0.277 | 1.534 | 26.016 | 68.639 | 0.071 | 0.084 | 0.100 | 0.244 | 0.009 | 0.000 |
| 2 | 350 | 0.086 | 0.330 | 0.651 | 2.594 | 28.636 | 61.229 | 0.186 | 0.265 | 0.180 | 0.336 | 0.042 | 0.014 |
| 3 | 250 | 0.035 | 0.011 | 0.028 | 0.158 | 25.460 | 66.734 | 0.030 | 0.017 | 0.013 | 0.016 | 0.000 | 0.000 |

TABLE 4

Isomerization of 2-methyl-2-pentene by MIL-101(Cr) with $F_4$-PBPA

| Time/hr | Temp. | $C_1$-$C_5$ | 4MP = 1 | c-4MP = 2 | t-4MP = 2 | 2MP = 1 | 2MP = 2 | c-3MP = 2 | t-3MP = 2 | 23DMB = 1 | 23DMB = 2 | 2EB = 1 | t-2H = |
|---|---|---|---|---|---|---|---|---|---|---|---|---|---|
| 0.08 | 250 | 0.135 | 2.068 | 3.100 | 11.588 | 20.496 | 53.643 | 1.905 | 3.182 | 0.695 | 1.925 | 0.393 | 0.100 |
| 1 | 250 | 0.029 | 0.119 | 0.295 | 1.470 | 26.546 | 69.999 | 0.101 | 0.115 | 0.067 | 0.175 | 0.013 | 0.000 |
| 2 | 350 | 0.050 | 0.395 | 0.673 | 2.506 | 29.985 | 63.704 | 0.252 | 0.360 | 0.124 | 0.242 | 0.059 | 0.014 |
| 3 | 250 | 0.022 | 0.013 | 0.031 | 0.152 | 27.204 | 70.959 | 0.048 | 0.028 | 0.012 | 0.015 | 0.000 | 0.000 |

The invention claimed is:

1. A metal organic framework having the structure of MIL-101(Cr) and comprising phenylene-bisphosphonic acid linking ligands.

2. The metal organic framework of claim 1, further comprising a pore diameter of up to about 30 Å.

3. The metal organic framework of claim 1, wherein the phenylene-bisphosphonic linking ligand is a perfluoro-1,4-phenylene-bis(phosphonic acid) linking ligand.

4. A process for exchanging an organic linking ligand in the metal organic framework of claim 1, the process comprising:
   (a) providing a first metal organic framework comprising a three-dimensional microporous crystal framework structure comprising metal-containing secondary building units connected by first organic linking ligands comprising a benzene-dicarboxylate having a first bonding functionality with the secondary building units,
   (b) providing a liquid medium containing an organic compound capable of reacting with the secondary building units to produce second organic linking ligands having a second bonding functionality with the secondary building units different from the first bonding functionality; and
   (c) contacting the first metal organic framework with the liquid medium under conditions effective for the organic compound to react with the secondary building units in the first metal organic framework and exchange at least some of the first organic linking ligands with second organic linking ligands and produce a second metal organic framework.

5. The process of claim 4, wherein the first organic linking ligand is bonded to each secondary building unit through a monoprotic acid group.

6. The process of claim 4, wherein the second organic linking ligand is bonded to each secondary building unit through a polyprotic acid group.

7. The process of claim 6, wherein the second organic linking ligand is bonded to each secondary building unit through a diprotic acid group.

8. The process of claim 4, wherein the second organic linking ligand comprises a phenylene-bisphosphonic acid.

9. The process of claim 4, wherein the second organic linking ligand comprises perfluoro-1,4-phenylene-bis(phosphonic acid).

10. The process of claim 4, wherein the second metal organic framework is isostructural with the first metal organic framework.

11. The process of claim 4, wherein the first metal organic framework has the structure of MIL101(Cr).

12. An organic compound conversion process comprising contacting an organic compound-containing feed with a catalyst comprising the metal organic framework of claim 1.

13. An olefin isomerization process comprising contacting an olefin-containing feed with a catalyst comprising the metal organic framework of claim 1.

14. A metal organic framework comprising trigonal nodes of 3 chromium atoms and at least 6 oxygen atoms partially or fully interconnected by phenylene-bisphosphonic linking ligands.

15. The metal organic framework of claim 14, wherein the phenylene-bisphosphonic linking ligand is a perfluoro-1,4-phenylene-bis(phosphonic acid) ligand.

16. The metal organic framework of claim 15, wherein at least one of the phenyl groups of the phenylene-bisphosphonic ligand is substituted with one or more electron withdrawing groups.

* * * * *